United States Patent [19]

Cragoe, Jr. et al.

[11] 4,140,776

[45] Feb. 20, 1979

[54] N-PYRAZINECARBONYL-N'-ACYLGUANIDINES

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 833,860

[22] Filed: Sep. 16, 1977

[51] Int. Cl.$^2$ .................. C07D 241/14; A61K 31/505
[52] U.S. Cl. ...................................... 424/251; 544/376; 260/302 D; 260/346.2
[58] Field of Search ................ 260/250 BN; 424/251; 544/376

[56] References Cited

U.S. PATENT DOCUMENTS

| 3,240,780 | 3/1966 | Cragoe | 260/250 |
| 3,313,813 | 4/1967 | Cragoe | 260/250 |
| 3,359,269 | 12/1967 | Cragoe | 260/250 |
| 3,360,517 | 12/1967 | Cragoe | 260/250 |
| 3,410,850 | 11/1968 | Cragoe | 260/244 |
| 3,491,094 | 1/1970 | Cragoe | 260/250 |

FOREIGN PATENT DOCUMENTS 843644  3/1976  Belgium.

*Primary Examiner*—Donald G. Daus
*Assistant Examiner*—Lisa Jones
*Attorney, Agent, or Firm*—Michael C. Sudol, Jr.; Harry E. Westlake, Jr.

[57] ABSTRACT

The case involves novel N-pyrazinecarbonyl-N'-acylguanidines and processes for preparing same. The N-pyrazinecarbonyl-N'-acylguanidines are eukalemic agents possessing diuretic and natriuretic properties.

7 Claims, No Drawings

N-PYRAZINECARBONYL-N'-ACYLGUANIDINES

BACKGROUND OF THE INVENTION

The background to this invention U.S. Pat. No. 3,313,813 patented Apr. 11, 1967 and issued to Edward J. Cragoe, Jr., shows novel (3-amino-5,6-disubstituted pyrazinoyl)guanidine compounds. The compounds of the 3,313,813 patent are useful because they possess diuretic and natriuretic properties. They differ from most of the known, effective diuretic agents, however, in that the compounds of the 3,313,813 patent selectively enhance the excretion of sodium ions while simultaneously causing a decrease in excretion of potassium ions. The potassium loss, which is caused by known diuretics, often results in a severe muscular weakness. Since the compounds of the 3,313,813 patent prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing diuretic agents.

Applicants' instant compounds shown in Formula I subsequently differ from the compounds shown in U.S. Pat. No. 3,813,813, in that they have an acyl group or substituted acyl group on the guanidino group of the compounds in the stated U.S. Patent. Applicants have found that the acyl guanidino group changes the pharmaceutical action and utility of these compounds. It has been found in U.S. Pat. No. 3,313,813 that the pyrazinoylguanidine compounds therein described when coadministered with other diuretic agents known to enhance the elimination of potassium ions along with sodium ions, will maintain the potassium ion excretion at approximately the normal or control rate and thus overcome this undesirable property of other diuretic agents.

In actuality, applicants' compounds in the instant case as further described, accomplish the objective previously achieved by using a combination of the pyrazinoylguanidine compounds of the 3,313,813 patent with diuretic agents which cause elimination of sodium with concomitant excessive potassium elimination. Thus, the effect of introducing an acyl group to the pyrazinoylguanidine compounds of the 3,313,813 patent results in producing eukalemic saluretic agents. Since the compounds of the instant invention are thus eukalemic saluretic agents they constitute single entities which are useful for the treatment of edema and hypertension and other diseases or conditions known to be responsive to this therapy.

SUMMARY OF THE INVENTION

The instant case covers novel N-pyrazinecarbonyl-N'-acylguanidines and processes for making the same. The novel compounds of this invention are depicted in Formula I below.

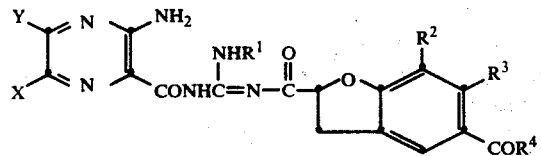

wherein $R^1$ is hydrogen or lower alkyl having from 1 to 5 carbon atoms such as methyl, ethyl, isopropyl, n-butyl or n-pentyl;

$R^2$ is methyl or halo, such as fluoro, chloro, bromo or iodo;

$R^3$ is hydrogen, methyl or halo, such as fluoro, chloro, bromo or iodo;

Y is amino, lower alkyl amino or di lower alkyl amino wherein the lower alkyl group have 1 to 4 carbon atoms;

X is halo, such as fluoro, chloro, bromo or iodo;

$R^4$ is thienyl or substituted thienyl wherein the substitutent is lower alkyl having 1 to 5 carbon atoms;
furyl or substituted furyl wherein the substituent is lower alkyl having 1 to 5 carbon atoms;
thiadiazoyl;
phenyl or
benzyl.

The compounds of this invention as shown by Formula I and the preferred compounds discussed above are useful because they possess diuretic and natriuretic properties. In addition, they are useful eukalemic saluretics, in other words, the compounds of the instant case cause neither loss or abnormal retention of potassium ions. In contradistinction, the pyrazinoylguanidine compounds of U.S. Pat. No. 3,313,813 do cause a decrease in the excretion of potassium ions. However, other well known diuretics such as furosemide, chlorthalidone and acetazolamide cause an increase in potassium excretion which often results in muscular weakness. Applicants' compounds combine in a single agent the advantages of a combination of the known pyrazinoylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristic of the diuretic.

The instant compounds disclosed herein contain an asymmetric carbon atom at position 2 of the benzofuran ring. This invention, therefore, embraces not only the racemic N-pyrazinecarbonyl-N'-acyl guanidines but also the optically active enantiomers. In general, the pure enantiomers are prepared by using an optically active benzofuran acid chloride as a starting material in the reaction scheme shown infra. The optically active benzofuran carboxylic acids from which the acid chlorides are prepared as described in Example 1 are known compounds.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the preferred compounds can be formed according to the process described below.

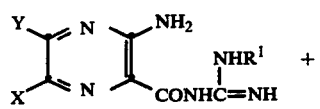

II

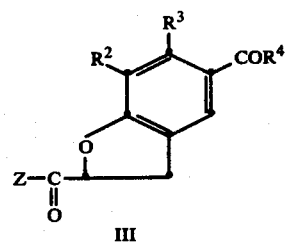

III

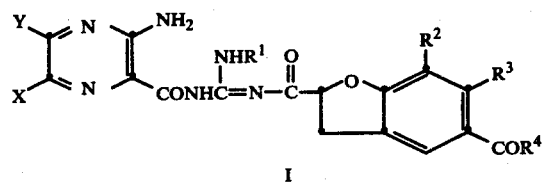

I wherein $R^1$, $R^2$, $R^3$, $R^4$, X and Y are as previously defined and Z is halo, preferably chloro.

In this process, a pyrazinoylguanidine (II) is reacted with a benzofurancarboxylic acid halide (III) or an isomer thereof to form the desired product (I). The reaction is usually run in an inert solvent such as acetonitrile, dioxane, tetrahydrofuran or benzene generally at a temperature of from room temperature to the reflux temperature of the particular inert solvent used.

Generally the reaction is also run in the presence of a hydrohalide acceptor such as triethylamine or pyridine to take up the HZ by-product of the reaction.

Although time is not critical the reaction is usually run at from 1 to 12 hours. Generally a 1 to 1 mole ratio of the reactants (II) and (III) are also used.

The desired product (I) can be isolated from the reaction mixture by known methods such as by filtration or concentration of the reaction mixture.

None of the reaction conditions described above are critical and they can be varied by those skilled in the art.

All the guanidine starting materials (II) used in the process described above are shown in and disclosed in U.S. Pat. No. 3,313,813 mentioned previously or at least can be obviously prepared from compounds disclosed in the aforementioned patent. The benzofurancarboxylic acid compounds from which the acid halides are prepared are described in Belgian Pat. No. 843,644 patented in Belgium on Dec. 30, 1976.

The acid halides can be prepared from the known benzofurancarboxylic acids by known methods in the art such as by reacting said acids with thionyl halide in an inert solvent (See Example 1). Generally the acid halides are not isolated, the reaction proceeding as described above.

Representative examples to illustrate this invention are the following:

EXAMPLE 1

1-(3,5-Diamino-6-chloropyrazinoyl)-2[6,7-dichloro-2,3-dihydro-5-(2-thenoyl)-2-benzofuroyl]guanidine 6,7-Dichloro-2,3-dihydro-5-(2-thenoyl)-2-benzofuran carboxylic acid (3.4 g.; 0.01M.) is combined with 2 ml. thionyl chloride and 50 ml. benzene. After 2 hours at reflux the excess thionyl chloride and benzene are removed by distillation at 20 mmHg to give 6,7-dichloro-2,3-dihydro-5-(2-thenoyl)-2-benzofuran carboxylic acid chloride as a yellow oil.

A solution of 3.8 g. of the acid chloride (0.01 M) and 25 ml. acetonitrile is added dropwise over 15 min. to a stirred suspension of 2.3 g. of N-amidino-3,5-diamino-6-chloro-2-pyrazinecarboxamide (0.01 M), 1 g. triethylamine (0.01 M) and 1 l. of acetonitrile. The reaction solution is refluxed 2 hours and distilled at 20 mmHg. to give a yellow solid. Recrystallization from DMF/$H_2O$ followed by recrystallization from dioxane/$H_2O$ gives pure 1-(3,5-diamino-6-chloropyrazinoyl)-2[6,7-dichloro-2,3-dihydro-5-(2-thenoyl)-2-benzofuroyl]-guanidine as a hemihydrate.

Calc.: C: 42.60; H: 2.68; N: 17.39; Found: C: 42.72; H: 2.63; N: 17.36.

EXAMPLE 2

1-(3,5-Diamino-6-chloropyrazinoyl)-2-(+)-[6,7-dichloro-2,3-dihydro-5-(2-thenoyl)-2-benzofuroyl]-guanidine By following substantially the procedure described in Example 1 but substituting for the 6,7-dichloro-2,3-dihydro-5-(2-thenoyl)-2-benzofuran carboxylic acid therein described an equimolar amount of the (+) isomer of 6,7-dichloro-2,3-dihydro-5-(2-thenoyl)-2-benzofuran carboxylic acid $[\alpha]_{436}^{25} = +11.5°$ (C, 1, acetone) there is obtained 1-(3,5-diamino-6-chloropyrazinoyl)-2-(+)-[6,7-dichloro-2,3-dihydro-5-(2-thenoyl)-2-benzofuroyl]guanidine.

Analysis for $C_{20}H_{14}Cl_3N_7O_4S$: Calc.: C, 43.29; H, 2.54; N, 17.67; Found: C, 43.22; H, 2.57; N, 17.64.

EXAMPLE 3

1-(3,5-Diamino-6-chloropyrazinoyl)-2-(−)-[6,7-dichloro-2,3-dihydro-5-(2-thenoyl)-2-benzofuroyl]guanidine hemihydrate By following substantially the procedure described in Example 1 but substituting for the 6,7-dichloro-2,3-dihydro-5-(2-thenoyl)-2-benzofuran carboxylic acid therein described an equimolar amount of the (−) isomer of 6,7-dichloro-2,3-dihydro-5-(2-thenoyl)-2-benzofuran carboxylic acid $[\alpha]_{436}^{25} = -11.5°$ (C, 1, acetone) there is obtained 1-(3,5-diamino-6-chloropyrazinoyl)-2-(−)-[6,7-dichloro-2,3-dihydro-5-(2-thenoyl)-2-benzofuroyl]guanidine hemihydrate.

Analysis for $C_{20}H_{14}Cl_3N_7O_4S \cdot \frac{1}{2} H_2O$; Calc.: C, 42.60; H, 2.68; N, 17.39; Found: C, 42.67; H, 2.73; N, 17.20.

EXAMPLE 4

By following the procedure described in Example 1 but substituting for the 6,7-dichloro-2,3-dihydro-5-(2-thenoyl)-2-benzofurancarboxylic acid an equimolar amount of the compounds shown in List 1 below there is obtained an equivalent amount of the respective compounds shown in List 2 below.

List 1

6,7-dichloro-2,3-dihydro-5-(2-furoyl)-2-benzofurancarboxylic acid;
6,7-dichloro-2,3-dihydro-5-(5-methyl-2-thenoyl)-2-benzofurancarboxylic acid;
6,7-dichloro-2,3-dihydro-5-(3-thenoyl)-2-benzofurancarboxylic acid;
6,7-dichloro-2,3-dihydro-5-(3-furoyl)-2-benzofurancarboxylic acid;
6,7-dichloro-2,3-dihydro-5-(5-methyl-2-furoyl)-2-benzofurancarboxylic acid;
6,7-dichloro-2,3-dihydro-5-(1,2,5-thiadiazol-3-yl)-2-benzofurancarboxylic acid;
6,7-dichloro-2,3-dihydro-5-(phenylacetyl)-2-benzofurancarboxylic acid.

List 2

1-(3,5-diamino-6-chloropyrazinoyl)-2-[6,7-dichloro-2,3-dihydro-5-(2-furoyl)-2-benzofuroyl]guanidine;
1-(3,5-diamino-6-chloropyrazinoyl)-2-[6,7-dichloro-2,3-dihydro-5-(5-methyl-2-thenoyl)-2-benzofuroyl]guanidine;
1-(3,5-diamino-6-chloropyrazinoyl)-2-[6,7-dichloro-2,3-dihydro-5-(3-thenoyl)-2-benzofuroyl]guanidine;
1-(3,5-diamino-6-chloropyrazinoyl)-2-[6,7-dichloro-2,3-dihydro-5-(3-furoyl)-2-benzofuroyl]guanidine;
1-(3,5-diamino-6-chloropyrazinoyl)-2-[6,7-dichloro-2,3-dihydro-5-(5-methyl-2-furoyl)-2-benzofuroyl]guanidine;
1-(3,5-diamino-6-chloropyrazinoyl)-2-[6,7-dichloro-2,3-dihydro-5-(1,2,5-thiadiazol-3-yl)-2-benzofuroyl]guanidine;
1-(3,5-diamino-6-chloropyrazinoyl)-2-[6,7-dichloro-2,3-dihydro-5-(phenylacetyl)-2-benzofuroyl]guanidine.

EXAMPLE 5

By following the procedure described in Example 1 but substituting for the N-amidino-3,5-diamino-6-chloro-2-pyrazinecarboxamide an equimolar amount of the compounds shown in List 1 below there is obtained an equivalent amount of the respective compounds shown in List 2 below.

List 1

N-amidino-3-amino-5-methylamino-6-chloro-2-pyrazinecarboxamide;
N-amidino-3-amino-5-ethylamino-6-chloro-2-pyrazinecarboxamide;
N-amidino-3-amino-5-propylamino-6-chloro-2-pyrazinecarboxamide;
N-amidino-3-amino-5-isopropylamino-6-chloro-2-pyrazinecarboxamide;
N-amidino-3-amino-5-butylamino-6-chloro-2-pyrazinecarboxamide;
N-amidino-3-amino-5-dimethylamino-6-chloro-2-pyrazinecarboxamide;
N-amidino-3-amino-5-diethylamino-6-chloro-2-pyrazinecarboxamide.

List 2

1-(3-amino-5-methylamino-6-chloropyrazinoyl)-2-[6,7-dichloro-2,3-dihydro-5-(2-thenoyl)-2-benzofuroyl]guanidine;
1-(3-amino-5-ethylamino-6-chloropyrazinoyl)-2-[6,7-dichloro-2,3-dihydro-5-(2-thenoyl)-2-benzofuroyl]guanidine;
1-(3-amino-5-propylamino-6-chloropyrazinoyl)-2-[6,7-dichloro-2,3-dihydro-5-(2-thenoyl)-2-benzofuroyl]guanidine;
1-(3-amino-5-isopropylamino-6-chloropyrazinoyl)-2-[6,7-dichloro-2,3-dihydro-5-(2-thenoyl)-2-benzofuroyl]guanidine;
1-(3-amino-5-butylamino-6-chloropyrazinoyl)-2-[6,7-dichloro-2,3-dihydro-5-(2-thenoyl)-2-benzofuroyl]guanidine;
1-(3-amino-5-dimethylamino-6-chloropyrazinoyl)-2-[6,7-dichloro-2,3-dihydro-5-(2-thenoyl)-2-benzofuroyl]guanidine;
1-(3-amino-5-diethylamino-6-chloropyrazinoyl)-2-[6,7-dichloro-2,3-dihydro-5-(2-thenoyl)-2-benzofuroyl]guanidine.

EXAMPLE 6

By following the procedure described in Example 1 but substituting for the N-amidino-3,5-diamino-6-chloro-2-pyrazinecarboxamide an equimolar amount of the compounds shown in List 1 below there is obtained an equivalent amount of the respective compounds shown in List 2 below.

List 1

N-amidino-3,5-diamino-6-fluoro-2-pyrazinecarboxamide;
N-amidino-3,5-diamino-6-bromo-2-pyrazinecarboxamide;
N-amidino-3,5-diamino-6-iodo-2-pyrazinecarboxamide.

List 2

1-(3,5-diamino-6-fluoropyrazinoyl)-2-[6,7-dichloro-2,3-dihydro-5-(2-thenoyl)-2-benzofuroyl]guanidine;
1-(3,5-diamino-6-bromopyrazinoyl)-2-[6,7-dichloro-2,3-dihydro-5-(2-thenoyl)-2-benzofuroyl]guanidine;
1-(3,5-diamino-6-iodopyrazinoyl)-2-[6,7-dichloro-2,3-dihydro-5-(2-thenoyl)-2-benzofuroyl]guanidine.

What is claimed is:

1. A compound of the formula:

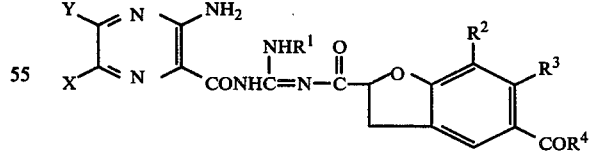

wherein
$R^1$ is hydrogen or lower alkyl having 1 to 5 carbon atoms;
$R^2$ is methyl or halogen;
$R^3$ is hydrogen, methyl or halogen;
$R^4$ is thienyl, thienyl monosubstituted by lower alkyl having 1 to 5 carbon atoms, furyl, furyl monosubstituted by lower alkyl having 1 to 5 carbon atoms, thiadiazoyl, phenyl or benzyl;

Y is amino, lower alkyl amino or di lower alkyl amino wherein the alkyl groups have 1 to 4 carbon atoms; and X is halogen.

2. A compound of the formula:

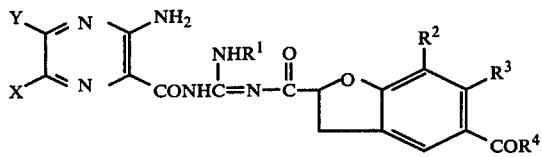

wherein $R^1$ is hydrogen or lower alkyl having 1 to 5 carbon atoms;

$R^2$ and $R^3$ are both chloro;

$R^4$ is thienyl or methyl thienyl;

Y is amino, lower alkyl amino or di lower alkyl amino wherein the lower alkyl group has 1 to 4 carbon atoms; and X is halogen.

3. A compound of claim 2 wherein $R^1$ is hydrogen;

X is chloro;

Y is amino;

$R^4$ is thienyl; which is 1-(3,5-diamino-6-chloropyrazinoyl)-2[6,7-dichloro-2,3-dihydro-5-(2-thenoyl)-2-benzofuroyl]guanidine.

4. The (+) isomer of the compound of claim 3.

5. The (−) isomer of the compound of claim 3.

6. A method of treating edema which comprises administering to a patient a pharmacologically acceptable dose of a compound of the formula:

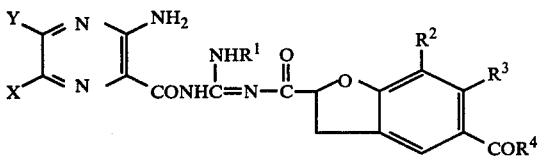

wherein $R^1$ is hydrogen or lower alkyl having 1 to 5 carbon atoms;

$R^2$ is methyl or halogen;

$R^3$ is hydrogen, methyl or halogen;

$R^4$ is thienyl, thienyl monosubstituted by lower alkyl having 1 to 5 carbon atoms; furyl, furyl monosubstituted by lower alkyl having 1 to 5 carbon atoms; thiadiazoyl, phenyl or benzyl;

Y is amino, lower alkyl amino or di lower alkyl amino wherein the alkyl groups have 1 to 4 carbon atoms; and X is halogen.

7. A pharmaceutical composition for use in the treatment of hypertension and edema consisting essentially as an active ingredient, of a compound of the formula:

wherein $R^1$ is hydrogen or lower alkyl having 1 to 5 carbon atoms;

$R^2$ is methyl or halogen;

$R^3$ is hydrogen, methyl or halogen;

$R^4$ is thienyl, thienyl monosubstituted by lower alkyl having 1 to 5 carbon atoms, furyl, furyl monosubstituted by lower alkyl having 1 to 5 carbon atoms, thiadiazoyl, phenyl or benzyl;

Y is amino, lower alkyl amino or di lower alkyl amino wherein the alkyl groups have 1 to 4 carbon atoms; and X is halogen.

* * * * *